United States Patent [19]

Caron et al.

[11] Patent Number: 5,047,011

[45] Date of Patent: Sep. 10, 1991

[54] PIERCING PIN TRANSFER DEVICE FOR CONTINUOUS AMBULATORY PERITONEAL DIALYSIS

[75] Inventors: Lois L. Caron; William L. Rudzena, both of McHenry, Ill.

[73] Assignee: Abbott Laboratories, Abbott Park, Ill.

[21] Appl. No.: 483,496

[22] Filed: Feb. 20, 1990

[51] Int. Cl.⁵ .............................................. A61M 5/00
[52] U.S. Cl. .................................... 604/29; 604/411; 141/330
[58] Field of Search ................................. 604/27–30, 604/80, 88, 411–414, 905, 407, 408; 141/248, 330; 222/83, 83.5, 129, 145

[56] References Cited

U.S. PATENT DOCUMENTS

| 4,405,315 | 9/1983 | Handt | 141/330 |
|---|---|---|---|
| 4,500,788 | 2/1985 | Kulin et al. | 604/411 |
| 4,541,829 | 9/1985 | Munsch et al. | 604/411 |
| 4,557,727 | 12/1985 | Handt | 141/330 |
| 4,614,514 | 9/1986 | Cerr et al. | 604/411 |
| 4,655,753 | 4/1987 | Bellotti et al. | 604/29 |
| 4,840,621 | 6/1989 | Lorkin et al. | 604/29 |

Primary Examiner—C. Fred Rosenbaum
Assistant Examiner—Chalin Smith
Attorney, Agent, or Firm—A. Nicholas Trausch; Clifford A. Dean

[57] ABSTRACT

An improved motorized transfer mechanism for use in a continuous ambulatory peritoneal dialysis apparatus (CAPD) is provided for automatically transferring a piercing pin from the clamped port of a used container of used dialysis solution to the clamped port of a container of fresh dialysis solution. The transfer mechanism is characterized by a track member extending between opposed aligned port mountings, an upstanding guideway adjacent to each port mounting and a rack formation located midway between the opposite ends of the track member. The rack formation is rotatably engageable with a circular gear sector secured to the spike carrier disposed within the guideways of the track member. The linear movement between the opposed ports of the spike carrier is performed by a motor-driven drive screw. The intermediate 180 degree rotational movement of the spike occurring when the rack formation of the track member engages the circular gear sector of the spike carrier, both inverts the spike and positions it adjacent an ultraviolet bulb for sterilization thereof.

6 Claims, 6 Drawing Sheets

PIERCING PIN TRANSFER DEVICE FOR CONTINUOUS AMBULATORY PERITONEAL DIALYSIS

BACKGROUND OF THE INVENTION

This invention relates to the field of medical devices and, more particularly, to a continuous ambulatory peritoneal dialysis apparatus (CAPD) in which an improved motorized transfer mechanism is provided for automatically transferring a piercing pin or spike from the clamped port of a container of used dialysis solution to the clamped port of a container of fresh dialysis solution in a manner such that any touch contamination of the spike by the patient effecting the transfer is minimized. The simplicity of operation, effectiveness and integrity of such an apparatus is of utmost importance as many patients undergoing continuous ambulatory peritoneal dialysis may be impaired by failing eyesight or by lessening of their physical strength and dexterity and such transfers may have to be effected by such patients as often as four times a day.

Such a CAPD apparatus is disclosed in U.S. Pat. No. 4,840,621 which issued June 20, 1989 to the same assignee to whom this application is assigned. Accurate alignment of the spike with the port of the container of fresh dialysis solution is of utmost importance as is proper alignment of the spike with an ultraviolet bulb which serves to sterilize the spike during its transfer. As the present invention is directed to an improved and more accurate transfer mechanism for the CAPD apparatus disclosed in said U.S. Pat. No. 4,840,621, the disclosure of this patent is incorporated herein by reference.

SUMMARY OF THE INVENTION

The present invention is an improved transfer mechanism which is characterized by a track member which extends between aligned but opposed port mountings for the two solution containers and has upstanding guideways thereon adjacent each port mounting and, midway between the opposite ends of the track member, a rack formation. The spike carrier movement is controlled by a control member, to which it is secured, which has both a depending cam follower which is disposed within the aforesaid guideways and a circular gear sector which is rotatably engageable with the aforesaid rack formation. During linear movement of the spike carrier by a motor driven drive screw from the end of the track member adjacent the clamped port of the used solution container to the opposite end of the track member adjacent the clamped port of the fresh solution container, the initial linear withdrawal movement of the spike from the used solution container port and the final seal-piercing linear movement of the spike into the fresh solution container port are accurately controlled by movement of the cam follower between the upstanding guideways at opposite ends of the track member and the intermediate 180 degree rotational movement of the spike to both invert same and to position the spike adjacent an ultraviolet bulb for sterilization thereof is accurately controlled by engagement of the gear sector of the control member with the rack formation.

It is noted that the tip of the spike duplicates, in vertically spaced relationship, the movement of the cam follower relative to the track member.

Objects and advantages of the present invention will be apparent from the following description.

DETAILED DESCRIPTION OF THE PREFERRED EMBODIMENTS

Figure 1:
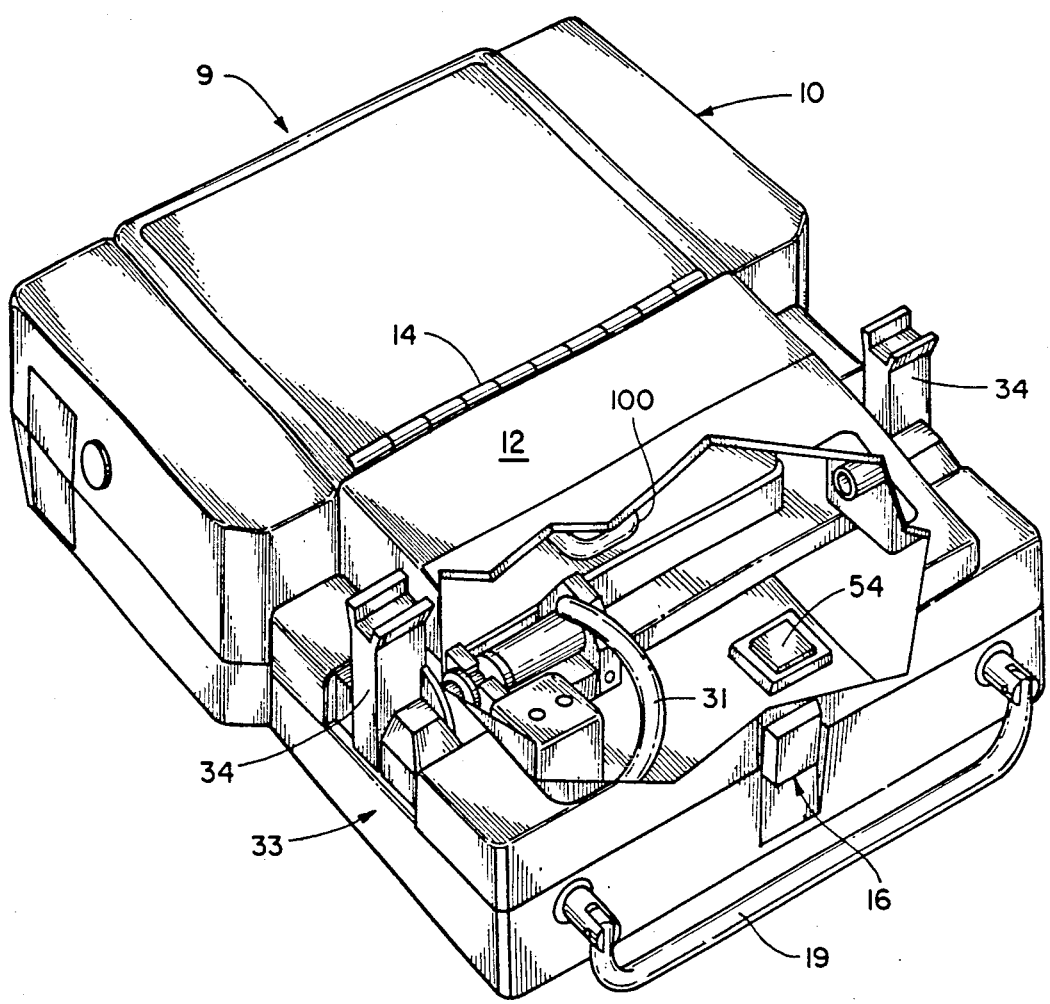
FIG. 1 is a perspective view of the continuous ambulatory peritoneal dialysis apparatus in which the transfer mechanism of the present invention is used with the lid broken away to show the spike in its left-hand position adjacent a port mount for a container of used dialysis solution.

Referring to FIG. 1 of the drawings, the transfer mechanism of the present invention is incorporated in a continuous ambulatory peritoneal dialysis apparatus 9 (CAPD) which is generally provide with a housing 10 having a lid 12. Lid 12 is connected to the housing by means of a hinge 14 so that lid 12 can be opened and closed. In the open position, access is permitted to the interior cavity. A latch 16 is provided for releasably securing the lid 12 in its closed position. For convenience, the device shown is equipped with a swing-out handle 19 so that the device can be easily carried.

The housing 10 can be made of various materials and can be formed by various means. It is advantageous, however, to form the housing of materials that are lightweight and resistant to breakage and corrosion, such as plastic or stainless steel. The housing is also preferably sized to be conveniently carried in one hand.

Figure 2:
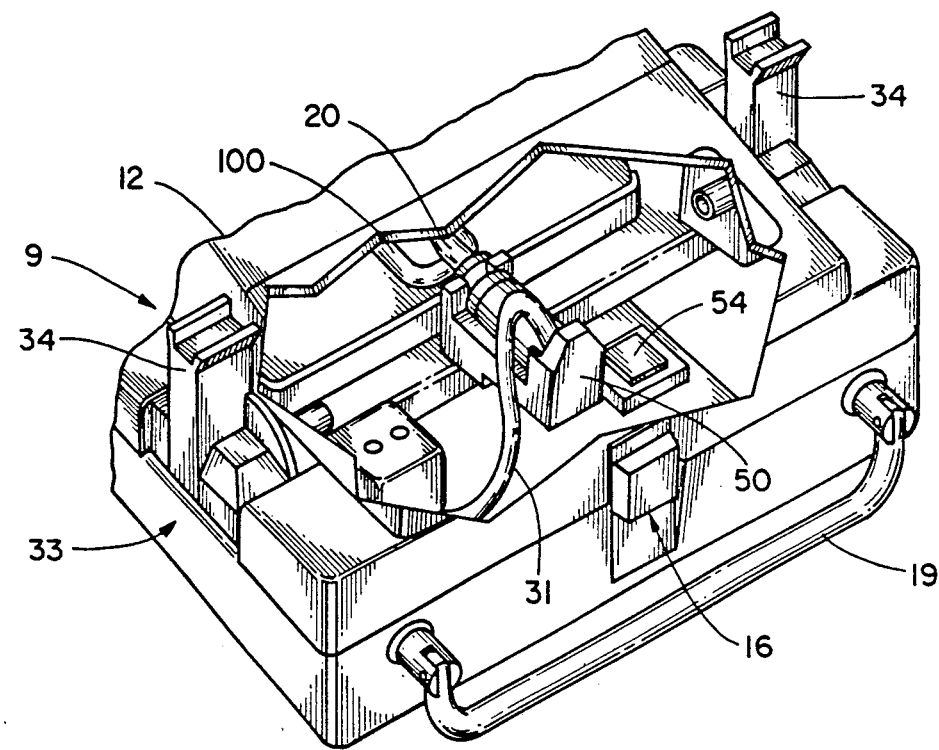
FIG. 2 is a fragmentary perspective view similar to FIG. 1 with the spike shown in its midpoint sterilization position adjacent an ultraviolet bulb of the CAPD apparatus.
Figure 3:
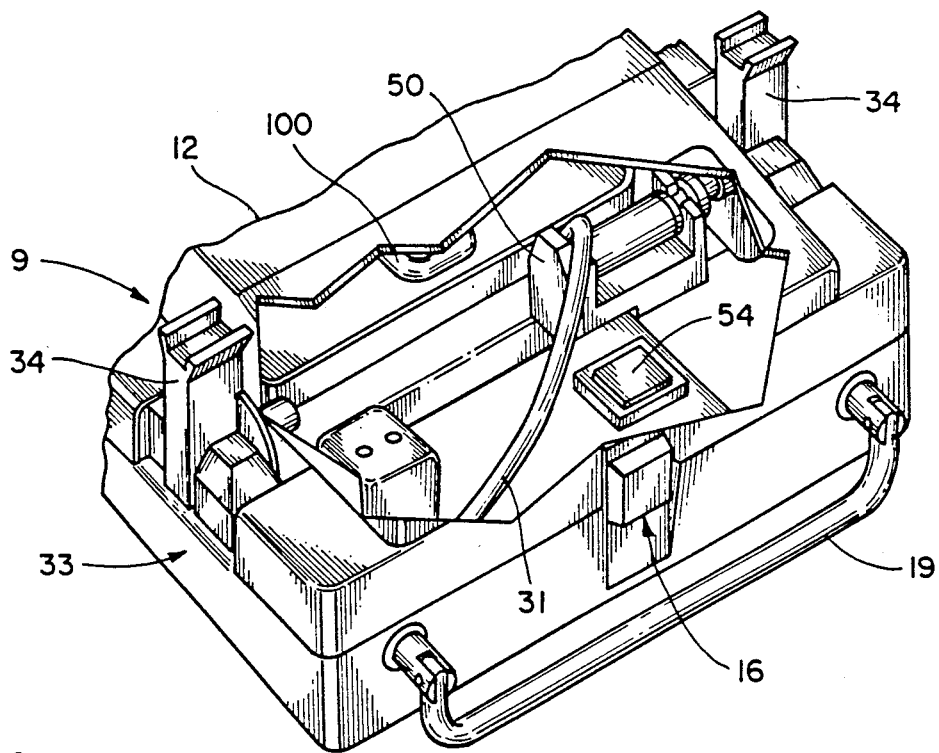
FIG. 3 is a fragmentary perspective view similar to FIGS. 1 and 2 with the spike shown in its right hand position adjacent a port mount for a container of fresh dialysis solution.
Figure 4:
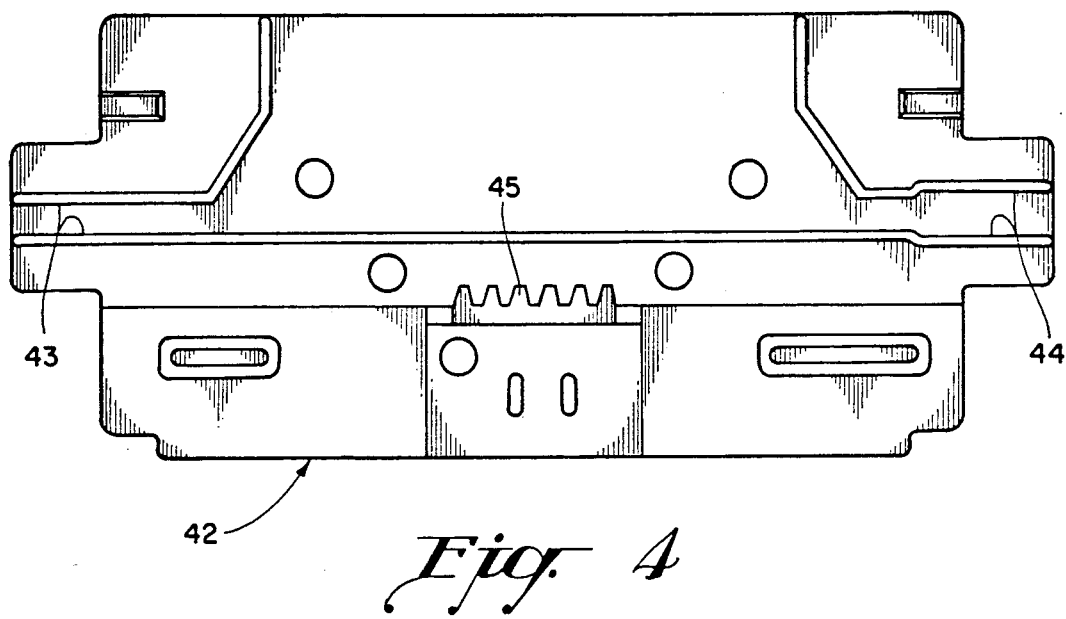
FIG. 4 is a top plan view of the track member of the transfer mechanism of the present invention.

With reference to FIGS. 1, 2 and 3, the specific application for which the CAPD 9 was developed is the transfer of a piercing pin 20 from a clamped port of a container of spent dialysis solution to a clamped port of a container of new dialysis solution. These dialysis solution containers are shown in the drawings of U.S. Pat. No. 4,840,621, the disclosure of which is incorporated by reference herein. Such containers of dialysis solution are commercially available, for example from Abbott Laboratories, Abbott Park, Ill. 60064. These containers have a capacity of approximately two liters.

Each bag of peritoneal dialysis solution is adapted to be held in place in one of the two port mounts 33 provided on opposite sides of the housing 10 in opposing alignment by a conventional clamp 34 (shown in FIGS. 1, 2 and 3).

As seen most clearly in FIGS. 6, 7, 8, 9 and 11, a hollow spike of piercing pin 20 has a pointed end 21 for piercing the seal of a container of fresh dialysis solution. The piercing pin 20 is attached to a flexible tubing set 31 which extends out of the housing 10 for connection to a catheter implanted in the patient's peritoneal cavity.

Figure 7:
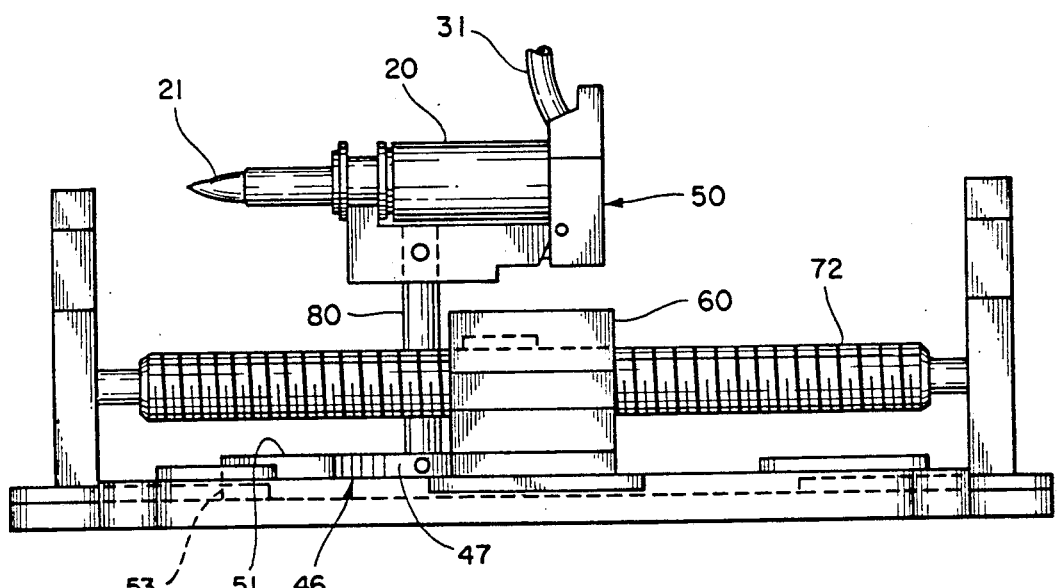
FIG. 7 is a front elevational view of the transfer mechanism of the present invention in the full-line position of FIG. 6.
Figure 8:
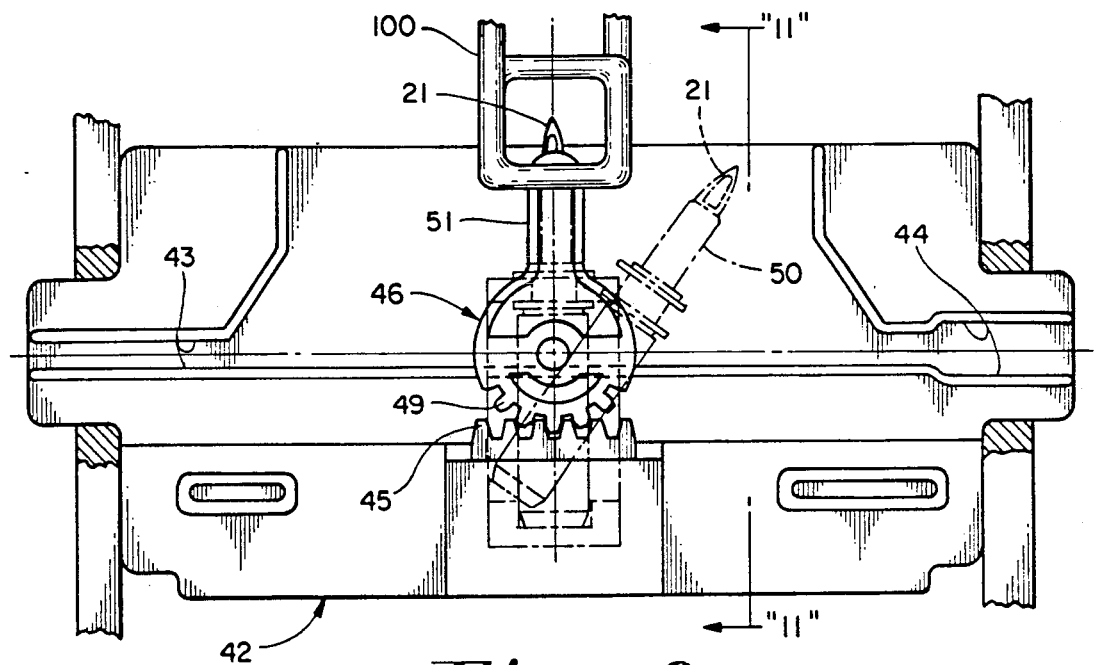
FIG. 8 is a top plan view similar to FIG. 6 with the spike shown in full line in its midpoint ultraviolet bulb sterilization position and in broken line at approximately the 135 degree position.
Figure 9:
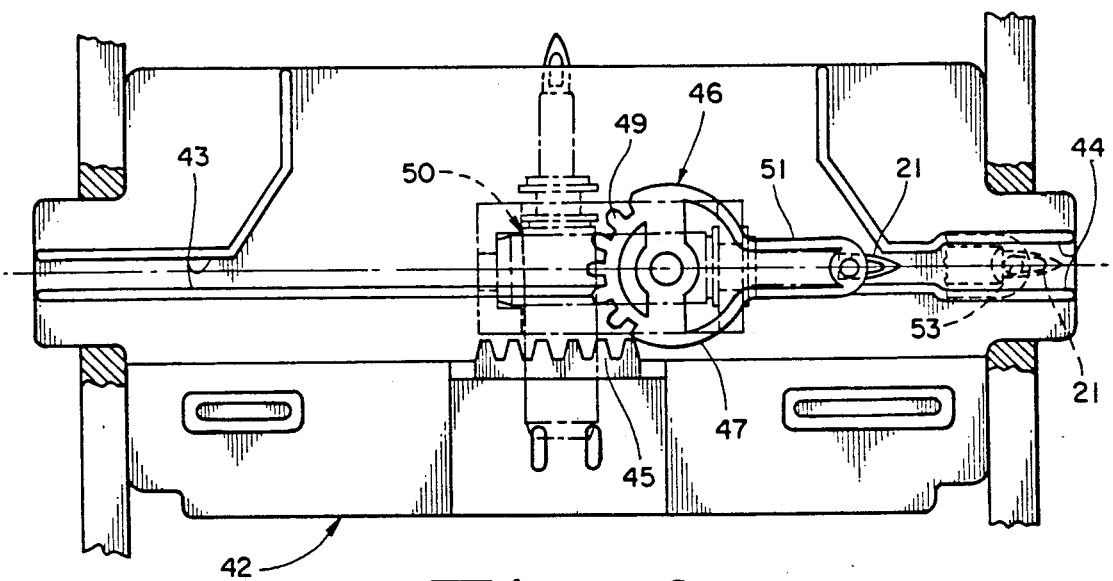
FIG. 9 is a top plan view similar to FIGS. 6 and 8 with the spike shown in full line in its "end of rotation" position and in broken line in its right-hand "finish" position for seal piercing connection with a container of fresh dialysis solution.
Figure 10:
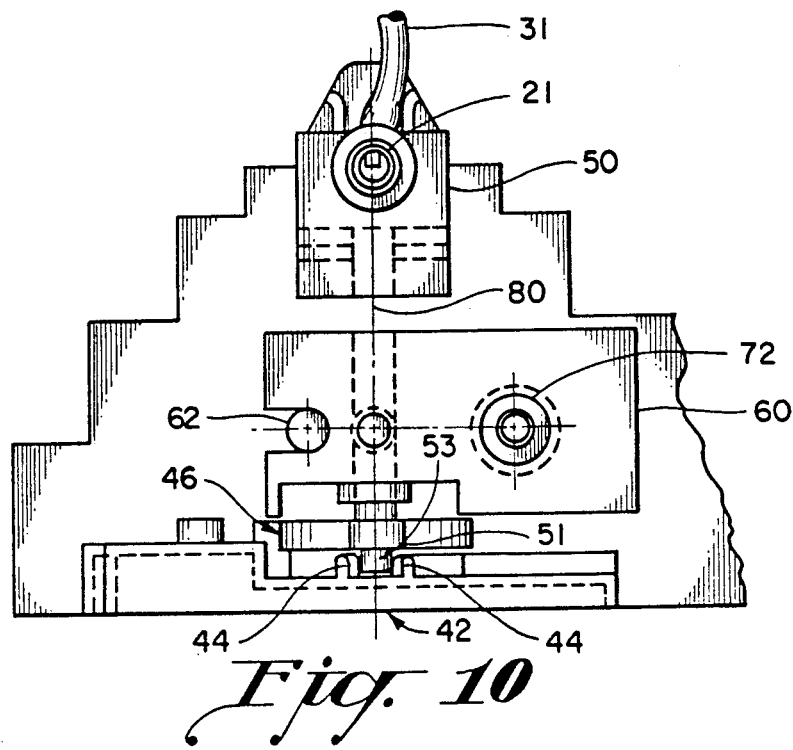
FIG. 10 is a right end elevational view of the transfer mechanism of the present invention as shown in FIG. 9.
Figure 11:
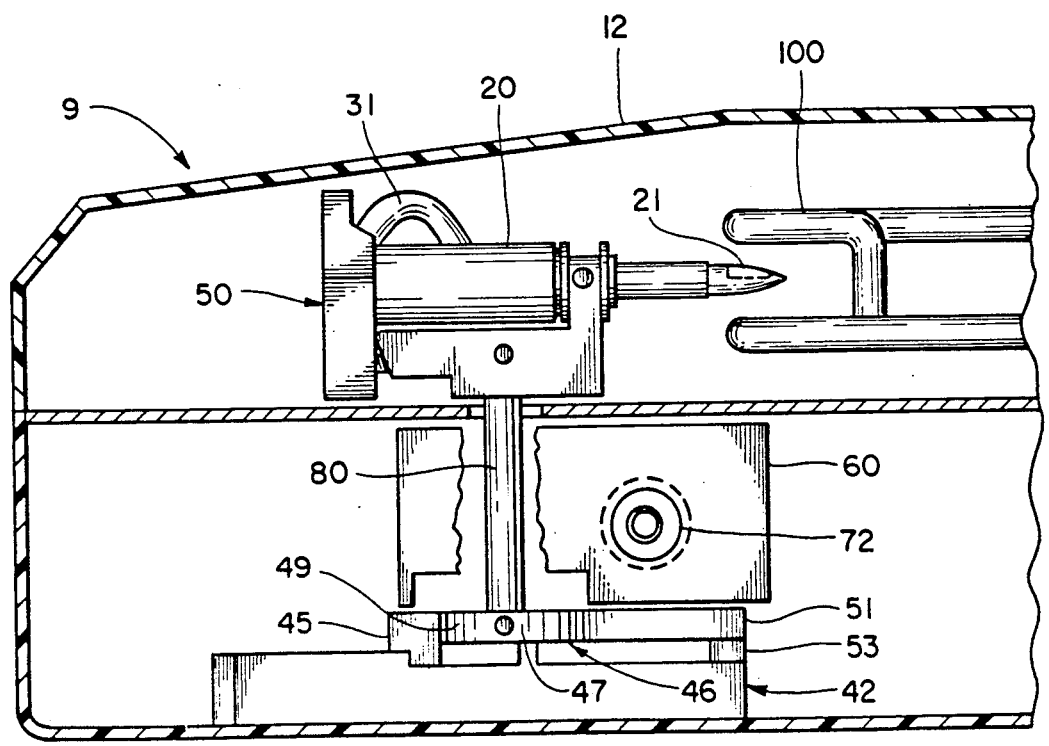
FIG. 11 is a fragmentary vertical sectional view taken generally along line 11—11 of FIG. 8.

With reference to FIGS. 7 and 11, in particular, a piercing pin carrier 50 is provided to hold the piercing pin 20. The piercing pin carrier 50 transfers piercing pin 20 from the port of the spent solution container to the opposing port of the fresh solution container. Piercing pin 20 is first disconnected from the spent container port, inverted approximately 180 degrees while moving from the spent container port to the fresh container port and into seal pierced engagement therewith. In the presently preferred embodiment, piercing pin or spike carrier 50 travels along a linear path from the two opposing ports. At an intermediate position between the two ports, the carrier 50 is rotated approximately 180 degrees about a vertical axis.

The linear and rotational movements of the spike carrier 50, and the hollow spike 20 mounted thereon, is controlled by the improved transfer mechanism best illustrated in FIGS. 4–11. A generally flat track member 42, which extends longitudinally between the aligned port mounts 33 for the two dialysis solution containers, is provided with upstanding guideways 43 and 44 which are disposed longitudinally at opposite ends of the track member 42 adjacent each of the port mounts 33. As will be discussed hereinafter, the spaced part, parallel guideways 43 and 44 accurately control the linear movements of the spike carrier 50 as it is initially withdrawn from the clamped port of the container of used dialysis solution and its final linear movement into seal-piercing engagement of the hollow spike 50 with the clamped port of the container of fresh dialysis solution. The previously mentioned 180 degree rotational movement of the spike carrier 50 between the aforesaid initial and final linear movements thereof is due in part to the provision of a toothed rack formation 45 which is provided on the track member 42 midway between the opposite ends thereof, as will be discussed further hereinafter.

The automatic transfer action described herein is provided by a program-controlled and motor-driven drive screw 72 which carries a drive block 60 and which is disposed parallel to and above the track member 42. Rotation of the drive screw 72 provides linear movement of the drive block 60 relative to the track member 42 in a known manner. A stabilizer rod 62, which extends parallel to the drive screw 72 and through the drive block 60, may be provided. A vertically disposed shaft 80 extends through the drive block 60 for movement therewith and for rotation relative thereto. The spike carrier 50 is mounted on and pinned to the upper end of the shaft 80 for rotation therewith and a control member 46 of the transfer mechanism is secured to the lower end of the shaft 80.

Figure 5:
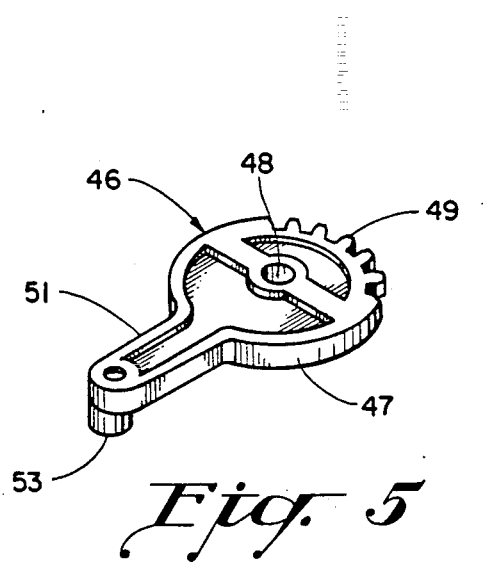
FIG. 5 is a perspective view of the control member of the transfer mechanism of the present invention.

The control member 46, as best illustrated in FIG. 5, is characterized by a circular portion 47 having a center bore 48 which is non rotatably mounted on the lower end of the shaft 80. The control member 46 is also characterized by a gear formation sector 49 and by a radial arm 51 which projects from the circular portion 47 at an angular position thereon which is diametrically opposite from the center of the gear formation sector 49. A cam follower 53 depends from the end of the radial arm 51 for confined engagement in the upstanding guideways 43 and 44.

Figure 6:
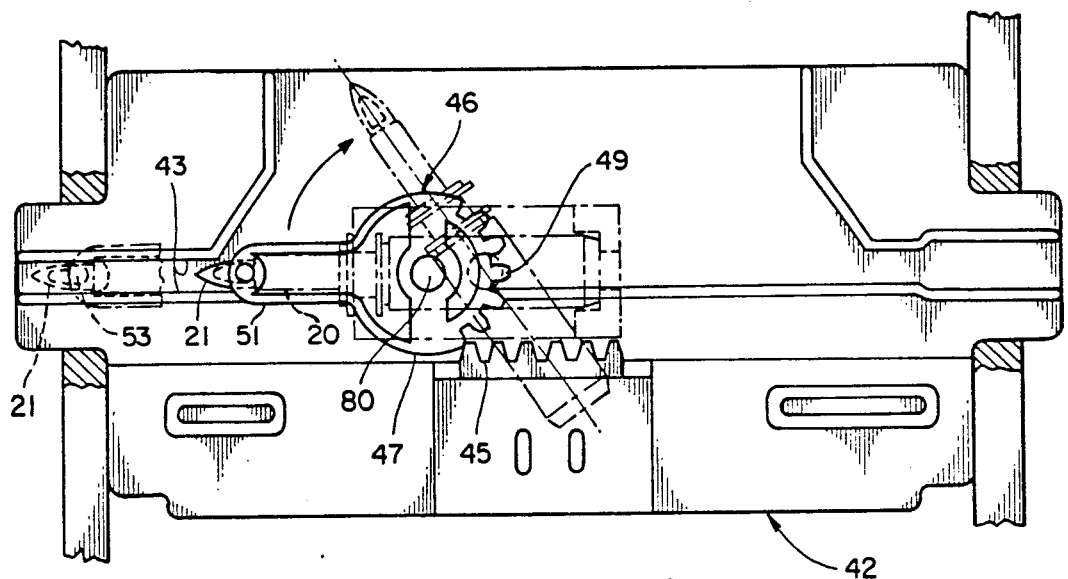
FIG. 6 is a top plan view of the transfer mechanism of the present invention with the spike and cam follower shown in broken line in their left hand "start" position, in full line at the beginning of their rotational movement, and again in broken line at approximately the 45 degree angle position.

The "start" or "home" position of the transfer mechanism of the present invention is to the left in the drawings adjacent the port mount 33 for the container of used solution with the spike being connected to the clamped port of the used solution container and the cam follower disposed in the guideway 43 (FIGS. 1 and 6). After the "start" button 54 has been pressed and the lid 12 closed, the drive block 60, the cam follower 53 of the control member 46, and the spike carrier 50 are moved to the right to withdraw the spike 20 from the container of spent solution with the linear movement being controlled by the cam follower 53 in the guideway 43, the diameter of the cam follower 53 being just slightly less than the width of the guideway 43. This linear movement to the right continues until the gear formation 45 (FIG. 6) whereupon the control member 46 and the spike carrier 50 are rotated clockwise through an angle of 90 degrees whereupon the spike 20 is disposed adjacent an ultraviolet bulb 100 for irradiated sterilization thereof. With the subject CAPD apparatus 9, the program controlled motor shuts off to provide a 30 second dwell period for the spike 20 adjacent the bulb 100. After the dwell period, the rotation continues for another 90 degrees (a total rotation of 180 degrees to invert the sterilized spike 20) until the gear formation 49 of the control member 46 disengages the rack formation 45 (FIG. 9) at which point the cam follower 53 and the guideway 44 provide linear movement of the carrier 50 to the right until the spike 20 has pierced a seal of a clamped port of a container of fresh solution.

It is noted that the guideway 44 is slightly wider than the guideway 43. This provides sufficient tolerance to insure proper piercing of the seal of the container of fresh solution by the spike 20 should it not be perfectly aligned in the port mount 33. After the spiked container of fresh solution has been removed from the CAPD apparatus 9, the programmed transfer mechanism automatically returns the spike carrier 50 to its left hand "start" or "home" position. The entire transfer time for the transfer mechanism disclosed herein should be approximately 1½ to 2 minutes.

Conventional safety interlocks may be used so that the UV bulb 100 is shut off if lid 12 is opened. Likewise, a system may be provided which is responsive to the the total UV energy supplied, so that the UV bulb is shut off when a prescribed amount of energy has been emitted. A light sensor may also be provided to communicate through a logic circuit with the lamp power supply, controlling the power supply to lamp 100, so that the UV light emitted provides a desired luminous flux.

The apparatus is powered by conventional rechargeable batteries, such as gel cell battery. The on/off switch 54 is accessible any time that the lid is closed. Once this switch is thrown, only failure of one of the safety checks will abort the transfer process. The unit checks for (1) adequate battery power to complete the entire transfer process; (2) proper placement of bags, clamps and connectors; (3) closure of the lid throughout the transfer; and (4) proper operation of the UV bulb. The unit identifies completion of the transfer by measuring motor current which is correlated with motor load. When the motor current reaches a value which indicates the piercing pin is completely seated in the bag port, the operation is terminated.

Although the preset invention has been described in connection with the presently preferred embodiment, those skilled in the art will recognize many modifications to sequence, arrangement, portions, elements, and materials which can be used in the practice of the invention without departing from its scope. It is intended that such changes and modifications be covered by the following claims.

We claim:

1. A transfer mechanism for a fully automated dialysis apparatus wherein a hollow seal-piercing spike is automatically linearly disengaged from a container of used dialysis solution, then rotated 180 degrees past an ultraviolet bulb for sterilization thereof, and then linearly moved into seal piercing engagement with a container of fresh dialysis solution, said transfer mechanism comprising a track member extending longitudinally between said used and fresh solution containers, upstanding longitudinally disposed guideways provided at the opposite ends of said track member, a rack formation provided midway between the opposite ends of said track member, a control member movable longitudinally of said track member and having a depending cam follower confinable in said guideways whereby to limit movement of said control member at the opposite ends of said track member to linear movements, a circular gear formation on said control member which, during said longitudinal movement of said control member, is engageable with said rack formation whereby said control member is rotated 180 degrees between said linear movements thereof, and means for connecting said hollow seal-piercing spike to said control member for linear and rotational movements therewith.

2. The transfer mechanism of claim 1 wherein said guideway at the end of said track member adjacent said container of fresh dialysis solution is wider than said guideway at the opposite end of said track member.

3. The transfer mechanism of claim 1 wherein a drive screw is provided for moving said control member longitudinally of said track member.

4. In a fully automated solution exchange, dialysis apparatus having a housing, a pair of port mounts disposed in axial alignment on opposite sides of said housing and adapted to receive the clamped ports of dialysis solution containers, an ultraviolet bulb in said housing, and a hollow, seal piercing spike connectable by flexible tubing to a dialysis patient, the improvement which comprises a transfer mechanism for automatically moving said spike from a container of used dialysis solution received in one of said port mounts into a dwell position adjacent said ultraviolet bulb for irradiation sterilization of said spike and then into seal piercing engagement with a container of fresh dialysis solution received in the other one of said port mounts to minimize the potential of touch contamination for said spike;

said transfer mechanism comprising a track member in said housing which extends between said pair of aligned port mounts, a motor-driven rotatable drive screw disposed parallel to said track member, upstanding cam guideways provided at the opposite ends of said track member adjacent each of said port mounts, a rack formation of gear teeth formed on said track member approximately midway between the ends of said track member, a drive block mounted on said drive screw for movement lengthwise of said drive screw during rotation thereof, a vertically disposed shaft extending through said drive block and being rotatable relative thereto, a cradle for said hollow seal-piercing spike secured to the upper end of said vertically disposed shaft, and a control member secured to the lower end of said vertically disposed shaft and disposed on said track member and having both a cam follower confined by said guideways at opposite ends of said track member and a gear formation engageable with said rack formation whereby during movement of said drive block from one end of said drive screw to the opposite end thereof said control member and said spike cradle are moved successively in a linear direction away from one of said port mounts, then rotated 180 degrees past said ultraviolet lamp, and then moved in a linear direction toward the other port mount, with a spike mounted in said cradle being automatically withdrawn from a container of used dialysis solution, sterilized by said ultraviolet bulb, and then piercingly engaged with a container of fresh dialysis solution.

5. The transfer mechanism of claim 4 wherein said guideway on said track member adjacent said port mount for the container of fresh solution is wider than said guideway adjacent the said port mount for the waste solution container to accommodate any minor misalignment of the clamped port of the fresh solution container in said port mount.

6. The transfer mechanism of claim 4 wherein said control member is characterized by a generally circular portion secured on the lower end of said vertically disposed shaft and having a gear formation thereon with the number of gear teeth corresponding to the number of gear teeth of said rack formation and by an arm extending radially from said circular portion diametrically opposite from the center of said gear formation and having a cam follower depending from the end thereof for engagement in said guideways provided at the opposite ends of said track member.

* * * * *